(12) United States Patent
Yokoyama et al.

(10) Patent No.: US 10,449,295 B2
(45) Date of Patent: Oct. 22, 2019

(54) SYRINGE ASSEMBLY

(71) Applicant: TERUMO KABUSHIKI KAISHA, Shibuya-ku, Tokyo (JP)

(72) Inventors: Kenji Yokoyama, Shizuoka (JP); Kunio Fukui, Shizuoka (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 549 days.

(21) Appl. No.: 14/987,242

(22) Filed: Jan. 4, 2016

(65) Prior Publication Data

US 2016/0113639 A1 Apr. 28, 2016

Related U.S. Application Data

(63) Continuation of application No. PCT/JP2013/068329, filed on Jul. 4, 2013.

(51) Int. Cl.
*A61M 5/19* (2006.01)
*A61M 5/315* (2006.01)
*A61B 17/00* (2006.01)

(52) U.S. Cl.
CPC .......... *A61M 5/19* (2013.01); *A61M 5/31596* (2013.01); *A61B 17/00491* (2013.01);
(Continued)

(58) Field of Classification Search
CPC ................ A61M 5/19; A61M 5/31511; A61M 5/31596; A61B 17/00491; A61B 2017/00495; A61B 2017/00522
See application file for complete search history.

(56) References Cited

U.S. PATENT DOCUMENTS 4,735,616 A * 4/1988 Eibl ................. A61B 17/00491
604/191
8,545,457 B2 * 10/2013 Hayakawa ............ B01F 5/0262
604/197
(Continued)

FOREIGN PATENT DOCUMENTS

JP 2009-131590 A 6/2009
JP 2009-240427 A 10/2009
(Continued)

OTHER PUBLICATIONS

Translation of JP 2009-240427, which was cited in the Information Disclosure Statement filed on Jan. 4, 2016. (20 pages).
(Continued)

*Primary Examiner* — Shefali D Patel
(74) *Attorney, Agent, or Firm* — Buchanan Ingersoll & Rooney PC

(57) ABSTRACT

A syringe assembly includes a first syringe having a first syringe outer cylinder filled with a first liquid, and a first gasket; a second syringe having a second syringe outer cylinder filled with a second liquid, and a second gasket; and a pusher assembly which performs a pushing operation of collectively moving the first and second gaskets. The pusher assembly includes a first pusher having a distal portion connected to the first gasket; a second pusher branching from the first pusher, extending distally, having a distal portion connected to the second gasket; and an operation section which is provided on a proximal-side extension line of the first pusher and is operated for the pushing operation.

11 Claims, 5 Drawing Sheets

(52) U.S. Cl.
CPC .............. *A61B 2017/00495* (2013.01); *A61M 5/31511* (2013.01)

(56) References Cited

U.S. PATENT DOCUMENTS

| | | | |
|---|---|---|---|
| 2009/0124986 A1 | 5/2009 | Hayakawa | |
| 2010/0310782 A1 | 12/2010 | Wawrzyniak et al. | |
| 2013/0331658 A1* | 12/2013 | Kai | A61B 17/00234 600/249 |
| 2017/0266367 A1* | 9/2017 | Fish | A61M 5/1408 |
| 2017/0281869 A1* | 10/2017 | Kai | A61M 5/2066 |
| 2017/0281870 A1* | 10/2017 | Kai | A61B 17/00491 |

FOREIGN PATENT DOCUMENTS

| | | | | |
|---|---|---|---|---|
| WO | WO-2012133067 A1 * | 10/2012 | ........ | A61M 5/31505 |
| WO | WO-2013070259 A1 * | 5/2013 | ............ | A61M 5/145 |

OTHER PUBLICATIONS

International Search Report (PCT/ISA/210) dated Aug. 1, 2013, by the Japanese Patent Office as the International Searching Authority for International Application No. PCT/JP2013/068329.

* cited by examiner

SYRINGE ASSEMBLY

CROSS-REFERENCES TO RELATED APPLICATIONS

This application is a continuation of International Application No. PCT/JP2013/068329 filed on Jul. 4, 2013, the entire content of which is incorporated herein by reference.

TECHNICAL FIELD

The present invention relates to a syringe assembly.

BACKGROUND DISCUSSION

A known method involves mixing two or more kinds of liquids together which are jetted to a target area to form an anti-adhesion material or a biological tissue adhesive applied to the target area. Applicators have been developed to employ this method to mix and jet components which solidify when mixed together, such as a solution containing thrombin and a solution containing fibrinogen. In such applicators, in order for the components to be applied to a target area while being mixed, the components are fed to a position in the vicinity of the target area in a separated state from each other.

One example of such an applicator is disclosed in Japanese Patent Laid-Open No. 2009-131590, and includes two syringes and a nozzle for mixing liquids supplied from the syringes and jetting the mixed liquid. In this applicator, each of the syringes includes a syringe outer cylinder having a mouth portion at a distal portion thereof, a gasket inserted in the syringe outer cylinder, and a pusher for moving the gasket. Spaces which are each surrounded by the syringe outer cylinder and the gasket are filled with individually different kinds of liquids. The pushers are connected to each other, and the pushers are collectively pushed by a pushing operation, whereby the gaskets are moved and the liquids are individually ejected from the mouth portions. The nozzle is connected to a gas supplying source which supplies sterile gas. The liquids ejected from the mouth portions are mixed together with the sterile gas, to be jetted together with the sterile gas.

There are many instances where the force required for moving the gaskets when discharging the liquids are different from each other. For example, the filled liquids may differ from each other in viscosity, or the syringe outer cylinders may differ from each other in inside diameter. Where there is a difference in magnitude between the forces required for moving the gaskets, the pusher of the syringe having the gasket which requires a smaller force for movement thereof is pushed preferentially. As a result, in each of the syringes, the pusher or the like will operate less smoothly during a pushing operation, making the pushing operation difficult to carry out. Furthermore, the resulting shaky operation of the pushers will cause the movement of the gaskets to become unsteady, possibly leading to nonuniform mixing of the liquids.

SUMMARY

A syringe assembly according to the present disclosure can help prevent a pusher assembly from wobbling or being rickety during a pushing operation and can help stabilize the discharge of the liquid.

(1) An embodiment of a syringe assembly includes: a first syringe including a first syringe outer cylinder which has a first mouth portion formed to project at a distal portion thereof and is filled with a first liquid, and a first gasket which is slidable within the first syringe outer cylinder and discharges the first liquid through the first mouth portion by a distal movement; a second syringe including a second syringe outer cylinder which has a second mouth portion formed to project at a distal portion thereof and is filled with a second liquid, and a second gasket which is slidable within the second syringe outer cylinder and discharges the second liquid through the second mouth portion by a distal movement; and a pusher assembly which performs a pushing operation of collectively moving the first gasket and the second gasket in a distal direction, wherein a force required for moving the first gasket when discharging the first liquid is greater than a force required for moving the second gasket when discharging the second liquid, and the pusher assembly includes a first pusher having a rectilinear shape and a distal portion connected to the first gasket, a second pusher branching from the first pusher, extending distally, having a distal portion connected to the second gasket, and an operation section provided on a proximal-side extension line of the first pusher and configured to be operated when performing the pushing operation.

(2) A further embodiment of a syringe assembly includes the syringe assembly as described in the above paragraph (1), wherein the second pusher branches from the first pusher at a boundary between the first pusher and the operation section.

(3) Further embodiments of a syringe assembly include the syringe assembly as described in the above paragraph (1) or (2), wherein the operation section is composed of a plate-shaped flange, which has a center on a center axis of the first pusher.

(4) Further embodiments of a syringe assembly include the syringe assembly as described in any one of the above paragraphs (1) to (3), wherein the second pusher has a curved portion where an intermediate portion in a longitudinal direction thereof is curved or bent, and its portion distally of the curved portion is parallel to the first pusher.

(5) Further embodiments of a syringe assembly include the syringe assembly as described in the above paragraph (4), wherein the operation section is composed of a disk-shaped flange, and a radius of the operation section is smaller than a separated distance between the center axis of the first pusher and a center axis of the portion of the second pusher which is located distally of the curved portion.

(6) Further embodiments of a syringe assembly include the syringe assembly as described in the above paragraph (4) or (5), wherein the portion of the second pusher which is located distally of the curved portion is contained in the second syringe outer cylinder when the liquid discharge is completed.

(7) Further embodiments of a syringe assembly include the syringe assembly as described in any one of the above paragraphs (1) to (6), wherein the first pusher is thicker than the second pusher.

(8) Further embodiments of a syringe assembly include the syringe assembly as described in any one of the above paragraphs (1) to (7), wherein the first liquid has a higher viscosity than the second liquid.

(9) Further embodiments of a syringe assembly include the syringe assembly as described in any one of the above paragraphs (1) to (8), wherein the first syringe outer cylinder has a greater inside diameter than the second syringe outer cylinder.

When a pushing operation is conducted, the gasket requiring a greater pushing force for movement thereof when discharging liquid can be primarily pushed by the first pusher. Further, the second pusher can be moved together with the first pusher by the same distance as the first pusher, so that the gasket requiring a smaller pushing force for movement thereof when discharging liquid can be pushed in a reliable manner. As a result, the pusher assembly can be prevented from wobbling during a pushing operation, and liquid can be discharged stably. In addition, where the center of the operation section is located on the center axis of the first pusher, the pushing force is transmitted effectively to the pusher assembly, so that liquid can be discharged more stably.

DETAILED DESCRIPTION

A syringe assembly according to the present disclosure will be described in detail below on the basis of a preferred embodiment illustrated in the accompanying drawings. Note that in the following, for convenience of description, the right side in FIGS. 2, 3, and 4 will be referred to as "proximal (side)," the left side as "distal (side)," the upper side as "upper (side)," and the lower side as "lower (side)."

Figure 1:
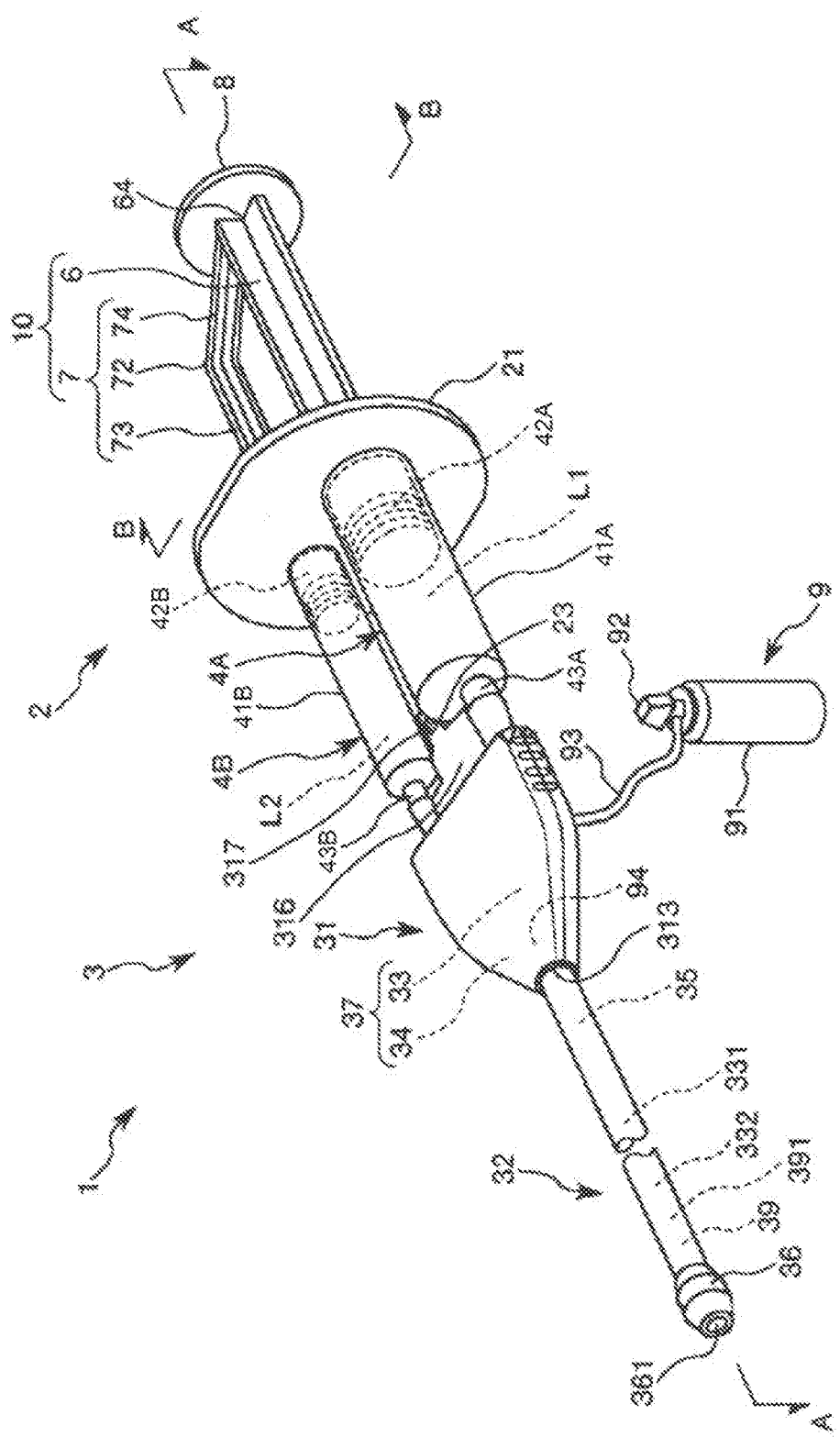
FIG. 1 is a perspective view showing a preferred embodiment of a syringe assembly.

As shown in FIG. 1, an applicator 1 is for applying while mixing two kinds of liquids (first liquid L1 and second liquid L2) differing in liquid composition. The applicator 1 includes: a syringe assembly 2 including a first syringe 4A filled with the first liquid L1, a second syringe 4B connected juxtaposedly with the first syringe 4A and filled with the second liquid L2, and a pusher assembly 10 which performs an operation to discharge each of the liquids (hereinafter this operation will be referred to as "pushing operation"); and a nozzle 3 by which liquid ejected from the syringe assembly 2 is ejected to an object of application. The nozzle 3 includes a nozzle main body 32 having a tubular shape, and a nozzle support section 31 which supports a proximal portion of the nozzle main body 32 and to which the syringe assembly 2 is connected.

The applicator 1 is configured to jet a mixture of the first liquid L1 and the second liquid L2 (hereinafter referred to as "mixture") together with sterile gas G (hereinafter referred to simply as "gas G") (see FIG. 2). By the gas G, the mixture is atomized (turned into a mist), whereby the mixture can be uniformly applied to a desired area (target area). The gas G is supplied from a gas cartridge (gas supplying means) 9. The gas cartridge 9 is connected to the nozzle 3 through a gas tube 93.

The gas cartridge 9 includes a cartridge main body 91 having an internal space in which the (compressed) gas G is filled at a high pressure, and an on-off cock 92 for controlling the supply of the gas G to the nozzle 3 or the stop of the supply. When applying the mixture, the cock 92 is used in an open state. Note that the gas G may be, for example, carbon dioxide.

Figure 2:
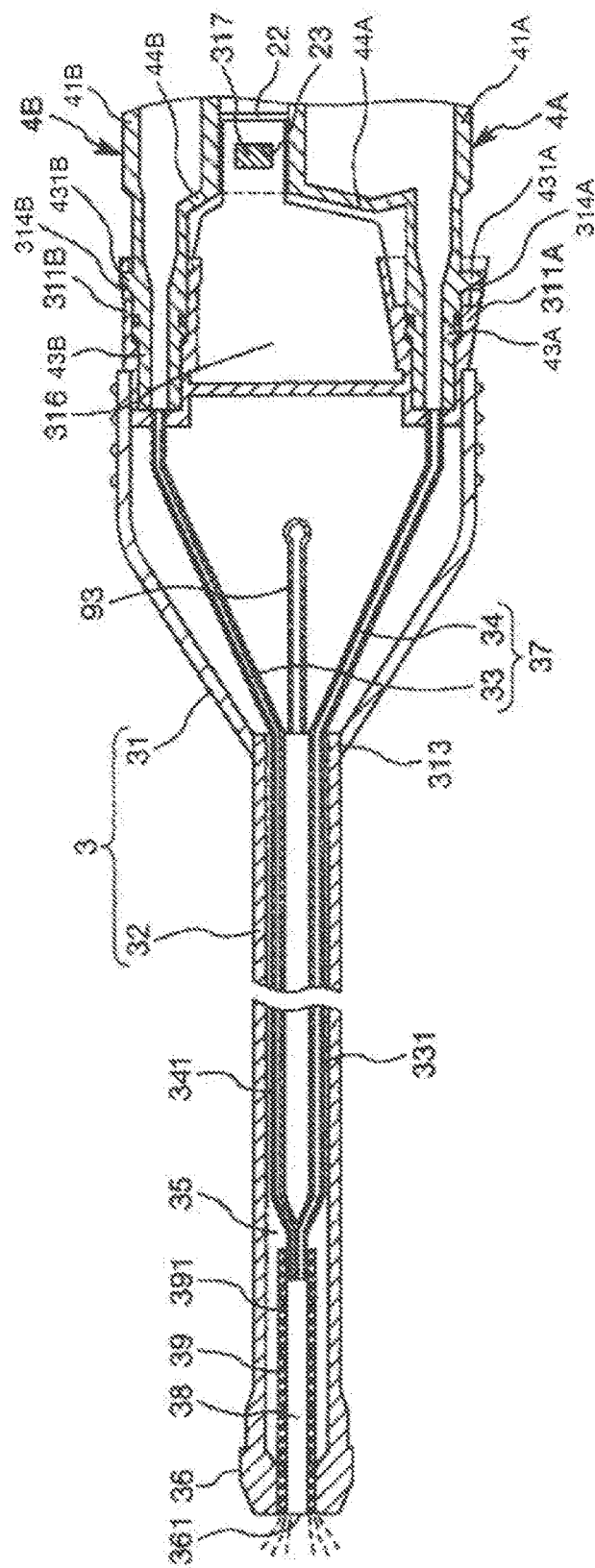
FIG. 2 is a sectional view taken along line A-A of FIG. 1.

As shown in FIG. 2, the nozzle support section 31 of the nozzle 3 includes a casing which is roughly triangular in external shape. The casing includes a first connection portion 311A for liquid-tight connection to a mouth portion 43A of the first syringe 4A, and a second connection portion 311B for liquid-tight connection to a mouth portion 43B of the second syringe 4B, and is formed with an opening portion 313 into which the nozzle main body 32 is inserted.

Since the first connection portion 311A and the second connection portion 311B are configured in substantially the same fashion, the first connection portion 311A will be described on a representative basis.

As depicted in FIG. 2, the first connection portion 311A is a portion which is tubular in shape and provided at a proximal portion of the nozzle support section 31 and into which the mouth portion 43A of a syringe outer cylinder 41A is inserted. In addition, the first connection portion 311A is provided with a hole 314A piercing from an inner periphery to an outer periphery thereof. A claw portion 431A of the mouth portion 43A is inserted into the hole 314A, whereby the first syringe 4A and the nozzle support section 31 are connected (fixed) to each other.

As shown in FIGS. 1 and 2, a projecting piece 316 having a plate-like shape and projecting proximally is provided between the first connection portion 311A and the second connection portion 311B. An engaging claw 317 is provided at a proximal portion of the projecting piece 316, and is inserted into an engaging hole 23 (described later) in the syringe assembly 2, whereby the syringe assembly 2 and the nozzle 3 are connected (fixed) to each other.

In addition, the opening portion 313 is provided at a distal portion of the nozzle support section 31, and a proximal portion of the nozzle main body 32 is inserted therein. In this inserted state, the nozzle main body 32 is fixed (supported) by the nozzle support section 31, through an adhesive, for example.

The nozzle support section 31 configured as above is formed from a material selected from, for example, various metallic materials or various resin materials.

As depicted in FIG. 2, the nozzle main body 32 is tubular in shape, and is provided at a distal portion thereof with a nozzle head 36 enlarged in outside diameter. Further, the nozzle main body 32 is provided at the distal thereof with a jet port 361, from which the mixture is jetted together with the gas G.

In addition, the nozzle main body 32 is provided therein with a liquid channel 37 composed of a first channel 33 through which the first liquid L1 flows and a second channel 34 through which the second liquid L2 flows. Further, the nozzle main body 32 is provided with a third channel 35 through which the gas G flows.

The first channel 33 is composed of a lumen of a first inner tube 331 inserted in the nozzle main body 32 and the nozzle support section 31. A proximal portion of the first inner tube 331 is connected liquid-tight to the first connection portion 311A of the nozzle support section 31, to communicate with the mouth portion 43A of the first syringe 4A through the first connection portion 311A.

The second channel 34 is composed of a lumen of a second inner tube 341 inserted in the nozzle main body 32 and the nozzle support section 31. A proximal portion of the second inner tube 341 is connected liquid-tight to the second connection portion 311B of the nozzle support section 31, to communicate with the mouth portion 43B of the second syringe 4B through the second connection portion 311B.

The first channel 33 and the second channel 34 have their distal portions approaching and joining each other. As a result, the liquid channel 37 can be provided with a confluence portion 38 where the first liquid L1 and the second liquid L2 come to flow together.

A distal portion 471 of a confluence portion side tube 39 is fitted in a distal inner peripheral portion of the nozzle head 36. In addition, a proximal portion of the confluence portion side tube 39 is fitted to distal portions of the first inner tube 331 and the second inner tube 341, which constitute the first channel 33 and the second channel 34, respectively. By this configuration, the confluence portion side tube 39 is reliably supported and fixed at both end portions thereof.

A pipe wall of the confluence portion side tube 39 is entirely composed of a gas-permeable membrane 391. The gas-permeable membrane 391 is permeable to the gas G present in the nozzle main body 32. This permits the gas G to flow into the confluence portion side tube 39 (the confluence portion 38) through the gas-permeable membrane 473. Therefore, the gas G having thus flowed in is jetted from the jet port 361 together with the first liquid L1 and the second liquid L2 having mixed with each other in the confluence portion 38 (see FIG. 2). Consequently, the mixture is turned into a mist and is applied to a target area.

Since the pipe wall of the confluence portion side tube 39 is entirely composed of the gas-permeable membrane 391 as described above, the gas G can flow into the confluence portion side tube 39 through the gas-permeable membrane 473 from any part in the circumferential direction of the confluence portion side tube 39. As a result, the gas G can be supplied into the confluence portion side tube 39 in the proper quantity, and, accordingly, the mixture jetted from the jet port 361 is reliably turned into a mist. With the mixture having been turned into a mist, it is ensured that the mixture becomes a uniform mixture of the first liquid L1 and the second liquid L2, and is applied to a target area in a favorable state (uniformly mixed state). When the ejection of the mixture is stopped, the gas G which has flowed in through the gas-permeable membrane 473 reliably pushes (blows) out the mixture in the confluence portion side tube 39 to the exterior. As a result, the mixture can be prevented from remaining in the jet port 361, so that the jet port 361 (nozzle 3) can be prevented from being clogged. In addition, leakage of residual liquid of the mixture (the first liquid L1 and the second liquid L2) from the jet port 361 can be reliably prevented.

The gas-permeable membrane 391 is formed with a multiplicity of pores (not depicted). Each of the pores pierces the gas-permeable membrane 391 in the thickness direction. The average pore diameter of these pores is set to be 0.01 µm to 0.45 µm, whereby it is ensured that the gas G can permeate the gas-permeable membrane 391 reliably and, at the same time, the gas-permeable membrane 391 is impermeable to bacteria. With the gas-permeable membrane 391 thus impermeable to bacteria, even if the gas G in the gas cartridge 9 is not in a sterile state, bacteria contained in the gas G are removed by the gas-permeable membrane 391, so that the bacteria are reliably prevented from flowing into the nozzle 3. Consequently, the mixture in a sterile state can be applied to a target area.

The membrane thickness (wall thickness) of the gas-permeable membrane 391 is not particularly limited, and is, for example, preferably 0.1 mm to 1 mm, more preferably 0.3 mm to 0.8 mm.

The surface area (area of the outer peripheral surface) of the gas-permeable membrane 391 is preferably 20 mm² to 200 mm², more preferably 40 mm² to 100 mm².

The gas-permeable membrane 391 is impermeable (water repellent) to the first liquid L1 and the second liquid L2, i.e., hydrophobic. For this reason, the first liquid L1 and the second liquid L2 in the confluence portion side tube 39 are reliably prevented from flowing back (flowing in) into the third channel 46 (confluence portion side tube 39) through the gas-permeable membrane 391. The gas-permeable membrane 391 can be formed from a hydrophobic material, or, alternatively, can have a surface thereof treated to be hydrophobic. The material (constituent material) which is hydrophobic may be, for example, polytetrafluoroethylene (PTFE).

The third channel 35 through which the gas G flows is composed of a gap defined between the first inner tube 331 (constituting the first channel 33) as well as the second inner tube 341 (constituting the second channel 34) and the nozzle main body 32 located on the outer periphery side of the inner tubes 331 and 341. A proximal portion of the nozzle main body 32 is connected to the aforementioned gas tube 93.

Thus, the nozzle 3 has a double pipe structure comprising the first inner tube 331 and the second inner tube 341 together with the nozzle main body 32. As a result, the first inner tube 331 and the second inner tube 341 are in a parallel positional relationship with the nozzle main body 32, so that the tubes can be favorably used as channels. Examples of the constituent materials for the tubes include various flexible or rigid resins such as polyvinyl chloride, polyethylene, polypropylene, etc., various rubber materials such as silicone rubber, etc., and various thermoplastic elastomers such as those based on polyurethane or the like.

The first syringe 4A and the second syringe 4B of the syringe assembly 2 are substantially the same in configuration, except for a difference in maximum internal volume (inside diameter). Therefore, the first syringe 4A will be described below on a representative basis. Note that the first syringe 4A is greater than the second syringe 4B in maximum internal volume (inside diameter).

Figure 3:
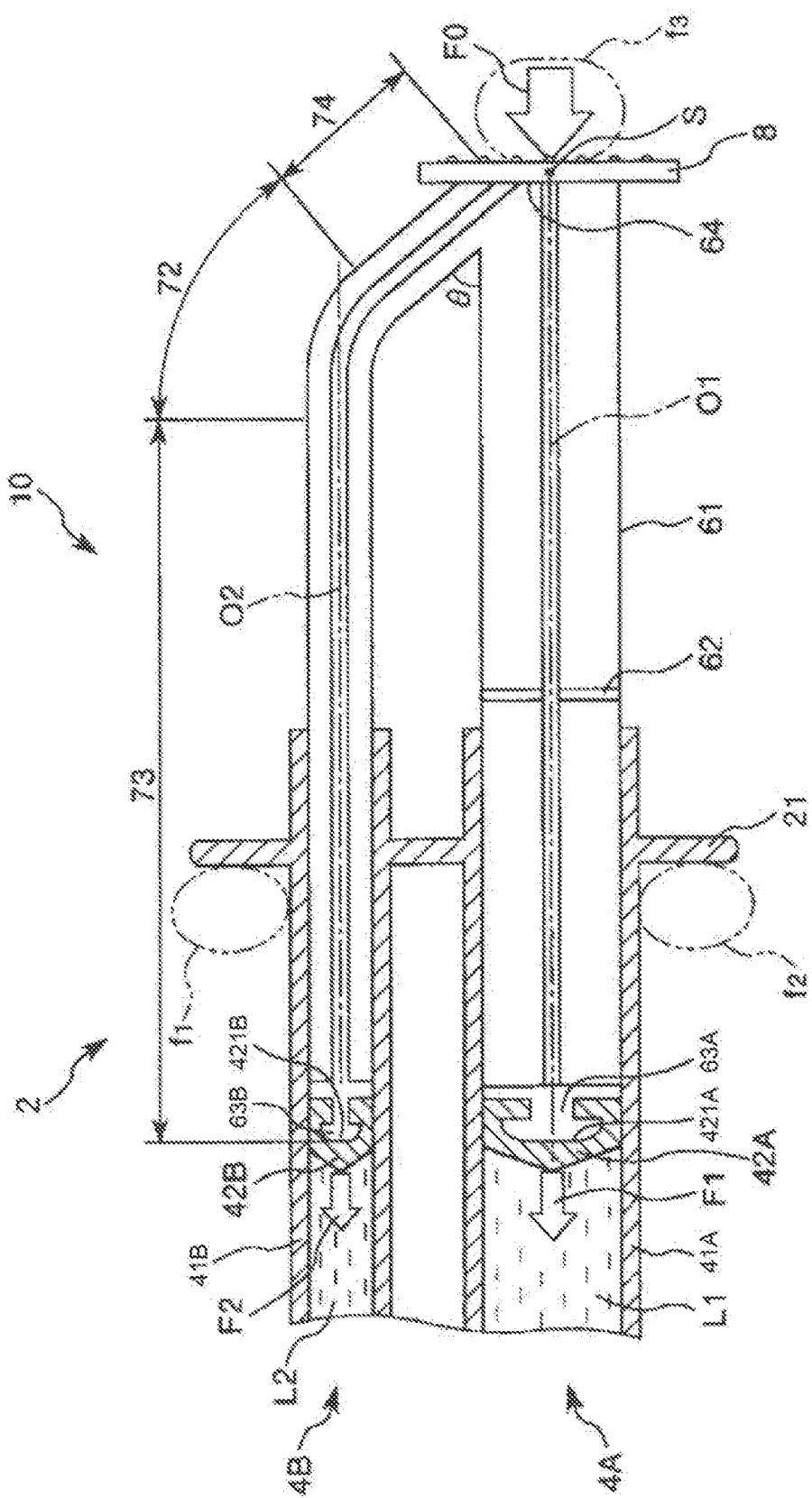
FIG. 3 is a view (partially sectional view) depicting an operating state of the syringe assembly shown in FIG. 1.
Figure 4:
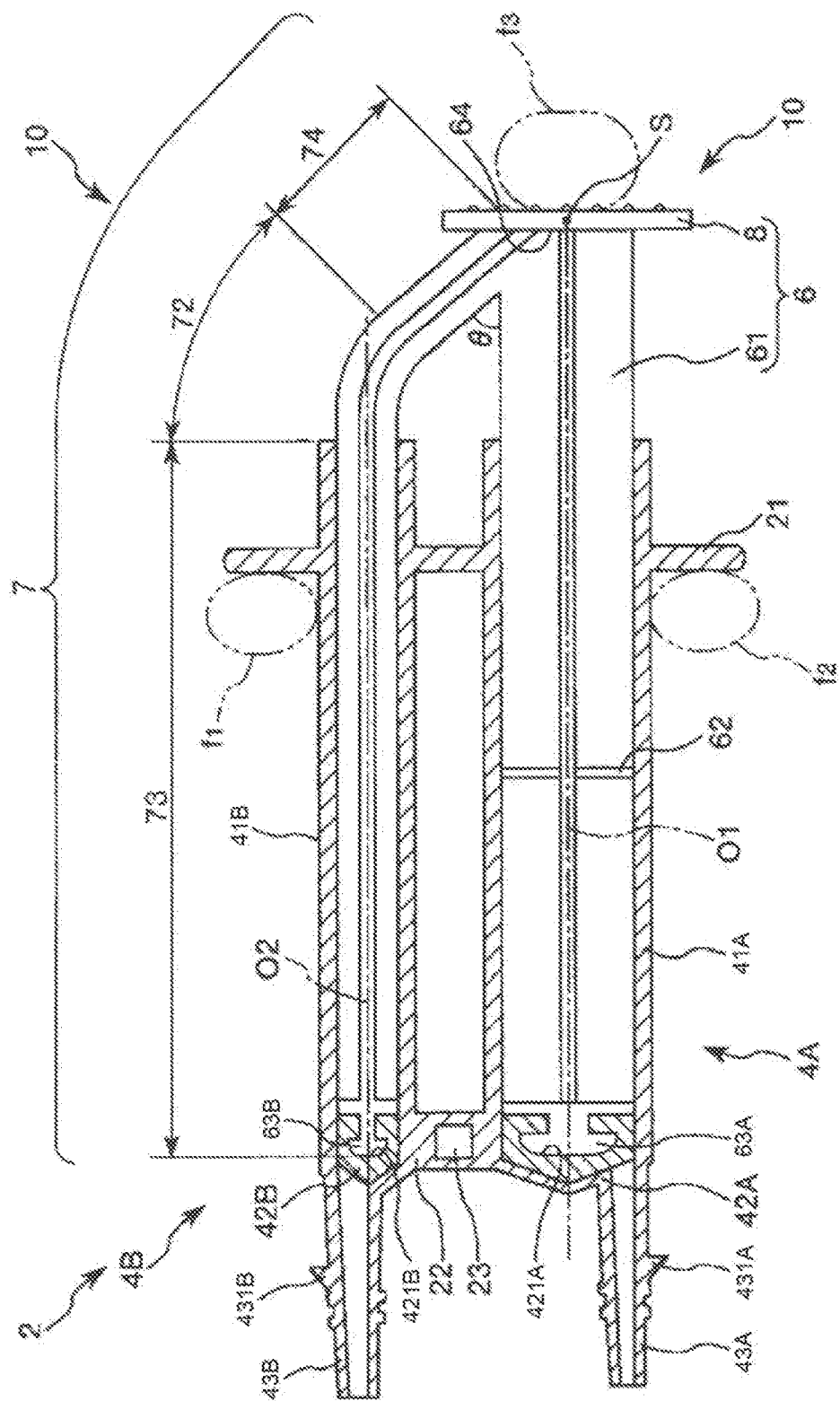
FIG. 4 is a view (partially sectional view) depicting an operating state of the syringe assembly shown in FIG. 1.

As shown in FIGS. 1, 3, and 4, the first syringe 4A includes a syringe outer cylinder 41A which is a first syringe outer cylinder, and a gasket 42A which is a first gasket.

The syringe outer cylinder 41A is in the form of a bottomed cylinder. The mouth portion 43A, which is a first mouth portion reduced in diameter as compared with a barrel portion of the syringe outer cylinder 41A, is formed to be integral with and to project from a bottom portion 44A of the syringe outer cylinder 41A. The mouth portion 43A has a cylindrical shape and is provided with a claw portion 431A at an outer peripheral portion thereof. The claw portion 431A is inserted into the hole 314A in the first connection portion 311A, whereby the syringe assembly 2 and the nozzle 3 are fixed.

At an outer circumference of an intermediate portion of the syringe outer cylinder 41A in the longitudinal direction, a flange 21 is integrally formed to project therefrom. The flange 21 is provided to range also to the outer periphery of a proximal end of the syringe outer cylinder 41B of the second syringe 4B, so that the first syringe 4A and the second syringe 4B are connected to each other in a juxtaposed relationship.

As shown in FIGS. 3 and 4, the syringe outer cylinders 41A and 41B are interconnected also by a plate piece 22 at outer peripheral portions of distal ends thereof. The plate piece 22 is provided with an engaging hole 23 piercing therethrough in the thickness direction. An engaging claw 317 of the nozzle 3 is inserted in the engaging hole 23, whereby the syringe assembly 2 and the nozzle 3 are fixed.

As the material constituting the syringe outer cylinders 41A and 41B, a resin such as polypropylene, cyclic polyolefin, polyesters, etc. is preferably used because of easy moldability and low water vapor permeability thereof. Note that the constituent material of each outer cylinder 41A and 41B is preferably substantially transparent, for ensuring visibility of the inside.

The gasket 42A formed from an elastic material is accommodated in the syringe outer cylinder 41A. The gasket 42A is formed at its outer peripheral portion with a plurality (e.g., two in the present embodiment) of ring-shaped projections along the whole circumference. These projections make close contact with and slide on the inner peripheral surface of the outer cylinder 41A, whereby liquid-tightness can be maintained more reliably and enhanced sliding properties can be realized.

As shown in FIGS. 3 and 4, the gasket 42A is formed with a hollow portion 421A opening in a proximal side thereof. In the hollow portion 421A is fitted a head portion 63A of a first pusher 6 of the pusher assembly 10 described later.

The constituent material of the gasket 42A, as well as gasket 42B discussed in detail below, is not specifically restricted. Examples of the material include elastic materials such as various rubber materials such as isoprene rubber, butadiene rubber, silicone rubber, etc., various thermoplastic elastomers based on polyurethane, polyester or the like, and their mixtures.

Like the first syringe 4A, the second syringe 4B includes a syringe outer cylinder 41B which is a second syringe outer cylinder and a gasket 42B which is a second gasket. With the gasket 42B moved distally, the second liquid L2 can be discharged from a mouth portion 43B of the syringe outer cylinder 41B which is a second mouth portion. Furthermore, the mouth portion 43B is formed to be integral with and to project from a bottom portion 44B of the syringe outer cylinder 41B. The mouth portion 43B has a cylindrical shape and is provided with a claw portion 431B at an outer peripheral portion thereof. The claw portion 431B is inserted into the hole 314B in the second connection portion 311B, whereby the syringe assembly 2 and the nozzle 3 are fixed.

Before being connected to the nozzle 3, the first syringe 4A is filled with the first liquid L1 in its space (liquid storage space) surrounded by the syringe outer cylinder 41A and the gasket 42A.

Like the first syringe 4A, the second syringe 4B is, before being connected to the nozzle 3, also filled with the second liquid L2 in its space (liquid storage space) surrounded by the syringe outer cylinder 41B and the gasket 42B.

The first liquid L1 and the second liquid L2 are suitably selected according to an application of the applicator 1, its intended use, a patient or the like. For example, for use in administration of a biological tissue adhesive, one of the first liquid L1 and the second liquid L2 may be a liquid (solution or the like) containing thrombin, while the other may be a liquid (solution or the like) containing fibrinogen.

For use in administration of an anti-adhesion material, one of the first liquid L1 and the second liquid L2 may be a liquid (solution or the like) containing carboxymethyl dextrin modified with a succinimidyl group, while the other may be a liquid (solution or the like) containing disodium hydrogen phosphate. The first liquid L1 and the second liquid L2 may therefore differ from each other in viscosity. In the present embodiment, the first liquid L1 is higher than the second liquid L2 in viscosity.

The first liquid L1 and the second liquid L2 in such a combination as this will gel (solidify) when mixed with each other. Owing to this change, the material resulting from the mixing of the first liquid L1 and the second liquid L2 (hereinafter referred to as "mixture") can reliably remain at biological tissue (target area) to which it has been applied. Furthermore, since the mixture can reliably remain in the target area, it can reliably function as a biological tissue adhesive or anti-adhesion material in the target area.

Note that the types and the combination of the first liquid L1 and the second liquid L2 are naturally not limited to the aforementioned ones.

In addition, the first syringe 4A is greater than the second syringe 4B in inside diameter. Further, the viscosity of the first liquid L1 filled in the first syringe 4A is higher than the viscosity of the second liquid L2 filled in the second syringe 4B. Meanwhile, the mouth portions 43A and 43B are the same in size. For these reasons in combination, a pushing force F1 required for moving the gasket 42A in the first syringe 4A when discharging the first liquid L1 is greater than a pushing force F2 required for moving the gasket 42B in the second syringe 4B when discharging the second liquid L2.

As shown in FIG. 3, in the syringe assembly 2, a pushing operation is conducted by pushing the pusher assembly 10 with a pushing force F0 which is the sum of the pushing force F1 and the pushing force F2, whereby the gaskets 42A and 42B are collectively moved. As a result of this, the syringe assembly 2 can discharge the first liquid L1 and the second liquid L2.

As shown in FIGS. 1, 3, and 4, the pusher assembly 10 includes a first pusher 6 connected to the gasket 42A, a second pusher 7 connected to the gasket 42B, and an operation section 8 provided on a proximal-side extension line of the first pusher 6. Now, each of these components will be described.

As depicted in FIGS. 1 and 3 to 5, the first pusher 6 has a first pusher main body 61 which is rectilinear in form and which has a cross-like cross-sectional shape.

As illustrated in FIGS. 3 and 4, the first pusher 6 is provided at an intermediate portion in the longitudinal direction thereof with a flange 62 as a reinforcement for the first pusher 6.

In addition, the first pusher main body 61 is formed at a distal portion thereof with the head portion (connection portion) 63A which is mushroom-like in shape. The head portion 63A is fitted in the hollow portion 421A of the gasket 42A of the first syringe 4A, whereby the gasket 42A of the first syringe 4A and the first pusher 6 are connected to each other.

Note that the method for connecting the first pusher 6 to the gasket 42 of the first syringe 4A is not limited to the one depicted in the drawings, and may for example be fixation (such as adhesion, fusion, etc.) or screwing or the like.

The second pusher 7 branches from a proximal portion of the first portion 6 and extends toward the distal side. The second pusher 7 is cross-like in cross-sectional shape, like the first pusher 6, and has a curved portion 72 where an intermediate portion in the longitudinal direction thereof is curved. As a result, the second pusher 7 can be divided into a rectilinear portion 73 which is the portion located distally of the curved portion 72 and a slant portion 74 which is a portion located proximally of the curved portion 72.

The slant portion 74 is rectilinear in form and is provided to be inclined with respect to the rectilinear portion 73 and the first pusher main body 61. The angle θ formed between the rectilinear portion 73 and the first pusher main body 61 is preferably an acute angle.

In addition, the slant portion 74 is connected to a boundary portion 64 between the first pusher main body 61 and the operation section 8. In other words, the boundary portion 64 constitutes a branching portion between the first pusher 6 and the second pusher 7. As a result, it is possible to omit that portion of the first pusher main body 61 which would be located proximally of the branching portion, in contrast to the case where the branching portion is located at an intermediate portion of the first pusher main body 61 in the longitudinal direction. Therefore, the first pusher main body 61 can be made as short as possible. Consequently, miniaturization of the pusher assembly 10 can be achieved.

The curved portion 72 is a portion which is curved toward the outer side. Since the angle θ formed between the slant portion 74 and the first pusher main body 61 is an acute angle, the curved portion 72 is located on the distal side as compared with the operation section 8. If the curved portion 72 is located at the same position as the operation section 8 or on the proximal side as compared to the operation section 8, then the user may perform a pushing operation by putting a finger on the curved portion 72 by mistake. In the pusher assembly 10, however, the operation section 8 is located on the distal-most side, which enables the user to push the operation section 8 in a reliable manner.

Furthermore, the curved portion 72 ensures that even if the user is about to perform a pushing operation on the curved portion 72 by mistake, the user's finger is not liable to be put on the second pusher 7. Therefore, the second pusher 7 can be so shaped that it is barely pushed from the proximal side. Accordingly, the user can push the operation section 8 more reliably, owing to the synergistic effect with the curved portion 72 being located on the distal side as compared to the operation section 8, as aforementioned.

Figure 5:
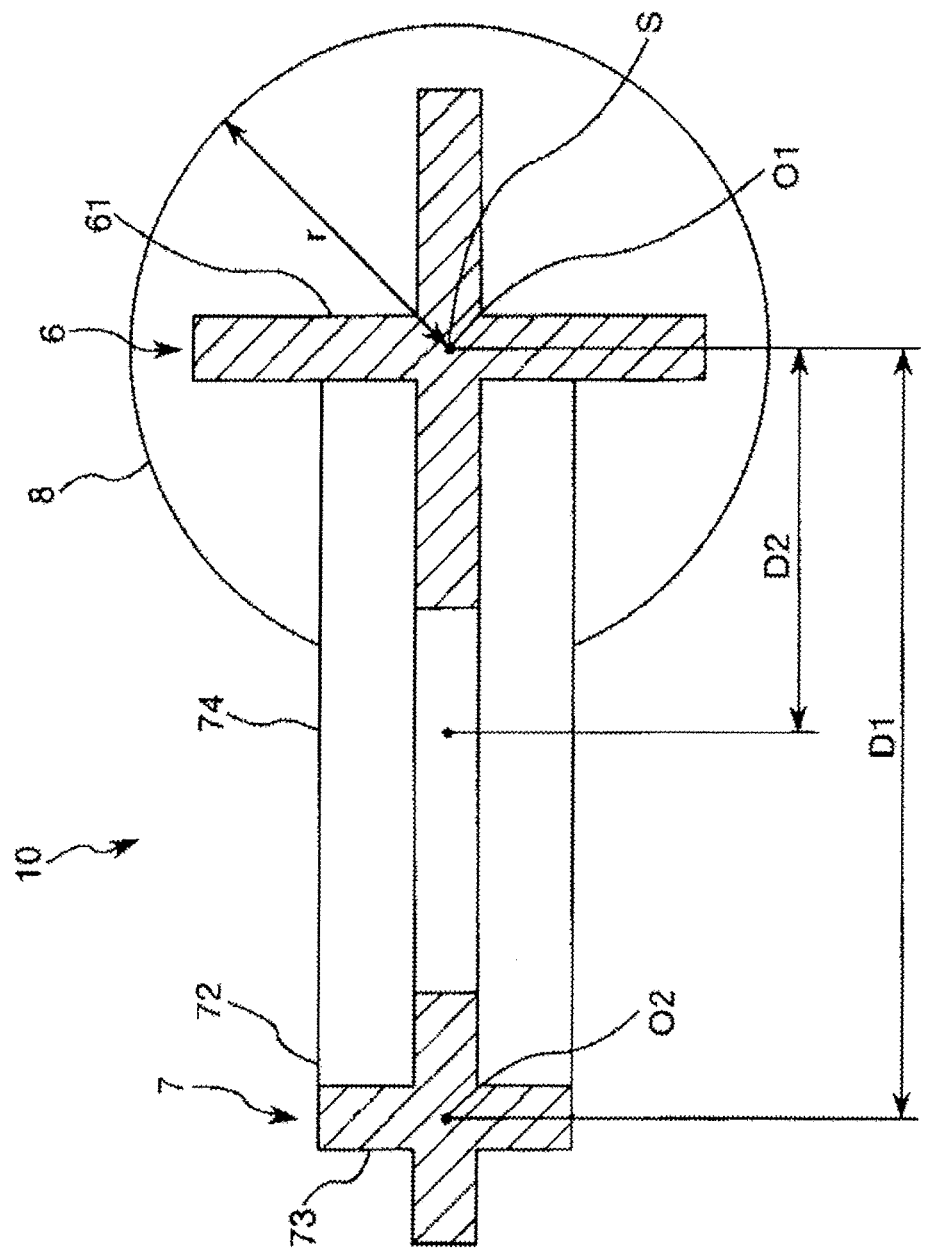
FIG. 5 is a sectional view taken along line B-B of FIG. 1.

The rectilinear portion 73 is provided in parallel to the first pusher main body 61. As shown in FIGS. 3 to 5, the rectilinear portion 73 is smaller than the first pusher main body 61 in thickness. In addition, the rectilinear portion 73 accounts for the majority of the second pusher 7. Furthermore, as depicted in FIG. 4, in a discharge completed state in which the discharge of the second liquid L2 has been completed, the rectilinear portion 73 accounting for the majority of the second pusher 7 is accommodated in the syringe outer cylinder 41B of the second syringe 4B. Accordingly, miniaturization of the syringe assembly 2 in the discharge completed state can be realized.

Note that a distal portion of the rectilinear portion 73 is configured similarly to the first pusher main body 61, and the gasket 42B of the second syringe 4B is connected thereto. In particular, the rectilinear portion 73 is formed at a distal portion thereof with the head portion (connection portion) 63B which is mushroom-like in shape. The head portion 63B is fitted in the hollow portion 421B of the gasket 42B of the second syringe 4B, whereby the gasket 42B of the second syringe 4B and the second pusher 7 are connected to each other.

As shown in FIGS. 1 and 3 to 5, the operation section 8 is composed of a disk-shaped flange. The operation section 8 is a section which is operated when performing a pushing operation. As depicted in FIG. 3, when performing a pushing operation, first, an index finger $f_1$ and a middle finger $f_2$ are put on the flange 21 connecting the syringe outer cylinders 41A and 41B, and a thumb $f_3$ is put on the operation section 8 to thereby grasp the syringe assembly 2. Next, as shown in FIG. 4, starting from the state of grasping the syringe assembly 2, the thumb $f_3$ is moved toward the index finger $f_1$ and the middle finger $f_2$ to thereby push the operation section 8 toward the distal side. In this manner, the user can perform a pushing operation.

In addition, as shown in FIGS. 3 to 5, the operation section 8 has its center S located on a center axis O1 of the first pusher main body 61. For this reason, the power point (the point where a force is exerted) of the pushing force F0 is located on the center axis of the first pusher main body 61. Consequently, the pushing force F0 is effectively transmitted to the first pusher 6 and the second pusher 7.

Furthermore, a radius r of the operation section 8 is preferably smaller than a separated distance D1 between the center axis O1 of the first pusher main body 61 and a center axis O2 of the rectilinear portion 73, more preferably smaller than a length D2 of one half the separated distance D1. With the operation section 8 sized as just mentioned, the user can be prevented from putting the thick of the user's thumb $f_3$ at a position spaced from the center S of the operation section 8, namely, on an edge portion of the operation section 8. Accordingly, the user can perform the pushing operation in a state in which the power point of the pushing force F0 is located at the center S of the operation section 8 with certainty.

Thus, in the pusher assembly 10, the operation section 8 is provided on the proximal-side extension line of the first pusher 6 connected to the gasket 42A, and, in addition, the second pusher 7 is provided to branch from the first pusher 6. For this reason, when the pushing operation is performed, a pushing force F1 accounting for the majority of the pushing force F0 is distributedly transmitted to the first pusher 6, while a pushing force F2 smaller than the pushing force F1 is distributedly transmitted to the second pusher 7. As a result, the gasket 42A is moved by the first pusher 6, and the gasket 42B is moved by the second pusher 7. Accordingly, the first liquid L1 and the second liquid L2 are discharged.

From the foregoing, it is seen that the pushing force F0 exerted on the operation section 8 can be transmitted to the first pusher 6 and the second pusher 7 in a in which it is distributed according to the ratio between the pushing force F1 and the pushing force F2 required for moving each of the gaskets 42A and 42B. Furthermore, a configuration is adopted in which the gasket 42A requiring a greater pushing force for movement thereof is pushed predominantly. Therefore, the gasket 42B requiring a smaller pushing force for movement thereof is prevented from being primarily pushed. As a result, wobbling of the pusher assembly 10 can be prevented, and the user can perform the pushing operation stably. Further, with the pusher assembly 10 prevented from being rickety, the moving distances of the gaskets 42A and 42B are equal, resulting in the mixing ratio between the liquids remaining constant.

Note that while the case of performing the pushing operation of pushing the pusher assembly toward the distal side has been described in the above embodiment, a similar effect to the aforementioned can be produced also in a sucking operation of sucking liquids into the syringe outer cylinders.

In addition, while the second pusher is composed of the rectilinear portion, the slant portion, and the curved portion in the above embodiment, a configuration may be adopted in which the slant portion is omitted and the rectilinear portion forms, on the proximal side thereof, a curved portion up to the first pusher. Furthermore, while the curved portion has a curved shape in the above embodiment, the curved portion may have, for example, a bent shape including a steep bend.

The detailed description above describes a syringe assembly. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A syringe assembly comprising:
a first syringe including a first syringe outer cylinder which has a first mouth portion formed to project at a distal portion thereof and is filled with a first liquid, and a first gasket which is slidable within the first syringe outer cylinder and discharges the first liquid through the first mouth portion by a distal movement;
a second syringe including a second syringe outer cylinder which has a second mouth portion formed to project at a distal portion thereof and is filled with a second liquid, and a second gasket which is slidable within the second syringe outer cylinder and discharges the second liquid through the second mouth portion by a distal movement; and
a pusher assembly which performs a pushing operation of collectively moving the first gasket and the second gasket in a distal direction,
wherein a force required for moving the first gasket when discharging the first liquid is greater than a force required for moving the second gasket when discharging the second liquid,
the pusher assembly includes a first pusher having a rectilinear shape and a distal portion connected to the first gasket, a second pusher branching from the first pusher, extending distally, having a distal portion connected to the second gasket, and an operation section provided on a proximal-side extension line of the first pusher and configured to be operated when performing the pushing operation,
the operation section is composed of a plate-shaped flange, which has a center on a center axis of the first pusher, and
the second pusher has a curved portion where an intermediate portion in a longitudinal direction thereof is curved or bent, and a portion of the second pusher distal of the curved portion parallel to the first pusher.

2. The syringe assembly according to claim 1, wherein a radius of the operation section is smaller than a separated distance between the center axis of the first pusher and a center axis of the portion of the second pusher which is located distally of the curved portion.

3. The syringe assembly according to claim 2, wherein the portion of the second pusher which is located distally of the curved portion is contained in the second syringe outer cylinder when the second liquid discharge is completed.

4. The syringe assembly according to claim 1, wherein the portion of the second pusher which is located distally of the curved portion is contained in the second syringe outer cylinder when the second liquid discharge is completed.

5. The syringe assembly according to claim 1, wherein the first pusher is thicker than the second pusher.

6. The syringe assembly according to claim 1, wherein the first liquid has a higher viscosity than the second liquid.

7. The syringe assembly according to claim 1, wherein the first syringe outer cylinder has a greater inside diameter than the second syringe outer cylinder.

8. A syringe assembly comprising:
a first syringe including a first syringe outer cylinder which has a first mouth portion formed to project at a distal portion thereof and is filled with a first liquid, and a first gasket which is slidable within the first syringe outer cylinder and discharges the first liquid through the first mouth portion by a distal movement;
a second syringe including a second syringe outer cylinder which has a second mouth portion formed to project at a distal portion thereof and is filled with a second liquid, and a second gasket which is slidable within the second syringe outer cylinder and discharges the second liquid through the second mouth portion by a distal movement; and
a pusher assembly which performs a pushing operation of collectively moving the first gasket and the second gasket in a distal direction,
wherein a force required for moving the first gasket when discharging the first liquid is greater than a force required for moving the second gasket when discharging the second liquid, and
the pusher assembly includes a first pusher having a rectilinear shape and a distal portion connected to the first gasket, a second pusher branching from the first pusher, extending distally, having a distal portion connected to the second gasket, and an operation section provided on a proximal-side extension line of the first pusher and configured to be operated when performing the pushing operation,
wherein the second pusher branches from the first pusher at a boundary between the first pusher and the operation section,
wherein the operation section is composed of a plate-shaped flange, which has a center on a center axis of the first pusher, and
wherein the second pusher has a curved portion where an intermediate portion in a longitudinal direction thereof is curved or bent, and a portion of the second pusher distal of the curved portion is parallel to the first pusher.

9. The syringe assembly according to claim 8, wherein a radius of the operation section is smaller than a separated distance between the center axis of the first pusher and a center axis of the portion of the second pusher which is located distally of the curved portion.

10. The syringe assembly according to claim 9, wherein the portion of the second pusher which is located distally of the curved portion is contained in the second syringe outer cylinder when the second liquid discharge is completed.

11. The syringe assembly according to claim 8, wherein the portion of the second pusher which is located distally of the curved portion is contained in the second syringe outer cylinder when the second liquid discharge is completed.

* * * * *